United States Patent [19]

Mueller et al.

[11] Patent Number: 4,539,415
[45] Date of Patent: Sep. 3, 1985

[54] PREPARATION OF 3-HYDROXYTETRAHYDROFURAN

[75] Inventors: Herbert Mueller, Frankenthal; Dieter Voges, Mannheim, both of Fed. Rep. of Germany

[73] Assignee: BASF Aktiengesellschaft, Fed. Rep. of Germany

[21] Appl. No.: 587,163

[22] Filed: Mar. 7, 1984

[30] Foreign Application Priority Data

Mar. 12, 1983 [DE] Fed. Rep. of Germany ....... 3308931

[51] Int. Cl.$^3$ ........................................... C07D 307/20
[52] U.S. Cl. .................................................. 549/475
[58] Field of Search ........................................ 549/475

[56] References Cited

U.S. PATENT DOCUMENTS 4,203,908 5/1980 Mueller et al. ...................... 549/509

FOREIGN PATENT DOCUMENTS 841592 4/1952 Fed. Rep. of Germany .

OTHER PUBLICATIONS

Organic Syntheses, New York, 1983 Collect., vol. 4, pp. 534–535.
Annalen der Chemie, 596, (1955), 112.

Primary Examiner—Richard L. Raymond
Attorney, Agent, or Firm—Keil & Weinkauf

[57] ABSTRACT

A process for the preparation of 3-hydroxytetrahydrofuran by catalytic dehydration of butane-1,2,4-triol, in which a catalyst chosen from the group of the bleaching earths is used and the dehydration is carried out in the presence of not less than 3 moles of water per mole of butane-1,2,4-triol.

3 Claims, No Drawings

PREPARATION OF 3-HYDROXYTETRAHYDROFURAN

The present invention relates to a process for the preparation of 3-hydroxytetrahydrofuran by dehydration of butane-1,2,4-triol.

3-Hydroxytetrahydrofuran is a valuable intermediate for syntheses of active ingredients. It is conventionally prepared from butane-1,2,4-triol by elimination of water, using an acid catalyst. Since butane-1,2,4-triol is prepared from but-2-ene-1,4-diol, which is itself a very valuable compound, it is essential for economically satisfactory preparation of 3-hydroxytetrahydrofuran that the dehydration be carried out with very high yield.

According to the literature data, yields of 80–95 mole % are achieved in the dehydration of butane-1,2,4-triol (cf. Organic Syntheses, New York, 1983 Collect. Vol. 4, pages 534–535, Annalen der Chemie, 596 (1955), 112, and German Pat. No. 841,592). However, the yields achievable in industrial operation of these processes do not exceed 90 mole %.

It is an object of the present invention to provide a process whereby the preparation of 3-hydroxytetrahydrofuran by dehydration of butane-1,2,4-triol may be carried out with yields greater than 95 mole %.

We have found that this object is achieved by the process according to the invention. In this novel process, 3-hydroxytetrahydrofuran is prepared by dehydration of butane-1,2,4-triol in the liquid phase over a catalyst at an elevated temperature, the catalyst being chosen from the group of the bleaching earths and the dehydration being carried out in the presence of not less than 3 moles of water per mole of butane-1,2,4-triol.

The dehydration of butane-1,2,4-triol is carried out in the liquid phase, using a suspended or fixed catalyst at an elevated temperature. The reaction rate depends on the chosen reaction temperature and on the amount of catalyst. For example, at 165° C. up to 5 parts of 3-hydroxytetrahydrofuran can be prepared from butane-1,2,4-triol per part by weight of catalyst per hour. The dehydration is advantageously carried out at 150°–200° C., preferably at 150°–180° C., in general at atmospheric pressure or slightly superatmospheric or reduced pressure. To achieve the desired high yield it is not necessary to maintain the low pressure of 30 mm Hg or less which the process disclosed in German Pat. No. 841,592 demands. This simplification is a further advantage of the novel process over the prior art.

According to the novel process, the catalyst used is chosen from the group of the bleaching earths. Bleaching earths, also referred to as fuller's earths, are colloidal hydrated aluminum hydrosilicates from the montmorillonite group, in which the aluminum ions can be partially replaced by iron or magnesium ions. The ratio of silica to alumina in these minerals is about 4:1. The bleaching earths are commercial products which are activated by acid treatment and are used extensively in refining edible oils and fats as well as mineral oils.

The amount of bleaching earth used is, for example, from 0.1 to 30, preferably from 5 to 20, % by weight based on butane-1,2,4-triol.

When using the said catalysts, it can be advantageous to add alkali metal carbonates or alkaline earth metal carbonates. The amount of such carbonates or of the corresponding bicarbonates added is from 0.1 to 1, advantageously from 0.3 to 0.9, % by weight based on the weight of catalyst. Depending on the origin of the catalyst modification with the said alkali metal compounds or alkaline earth metal compounds can under certain circumstances be dispensed with. Whether the addition of such compounds is or is not advisable is best established by laboratory experiments.

To achieve the object of the invention it is essential that the dehydration be carried out in the presence of not less than 3 moles of water per mole of butane-1,2,4-triol. Advantageously, from 5 to 20 moles of water per mole of triol are added. The object of the invention is not achieved if only the water formed by the dehydration reactions is present. Since the reaction temperature is as a rule above the boiling point of water the requisite amount of water can be introduced in the form of steam. However, it has proved particularly advantageous—and the reason for this is not immediately clear—to add the water in the form of a solution of the butanetriol. Since yields of above 90 mole % are only achieved when employing aqueous butanetriol solutions which contain not less than 60 mole % of water, the solution employed in general contains 40 mole % or less of butanetriol and 60 mole % or more of water. In general, economic considerations demand that the aqueous solution used should not contain less than 5 mole % of butanetriol.

The process can be carried out batchwise but is advantageously conducted continuously. A particularly advantageous method is to add the butanetriol to be converted, as an aqueous solution, with stirring and at the rate at which the reaction product and the water of reaction, as well as the additional water used as a reaction assistant, distil from the reaction vessel, for example via an appropriate fractionating column. In that case, the pure product, together with the water formed and the water introduced with the starting material, is as a rule obtained at the top of the column.

Using the novel process, 3-hydroxytetrahydrofuran is obtained in virtually quantitative yield. The process can moreover be carried out with as high a catalyst productivity as may be desired, and is environmentally particularly non-polluting. Since the reaction mixture does not contain any corrosive substances it is possible to use apparatus made from inexpensive materials such as the steel commonly used for chemical apparatus. It is not necessary to use lead-lined vessels which are needed, and industrially generally used, when carrying out the conventional reaction with sulfuric acid or with sulfonic acids. This advantageous outcome of the process was unexpected. In fact, if the instructions of European Pat. No. 1,291, in which a process for the preparation of tetrahydrofuran by dehydration of diols over bleaching earths is described, are followed 3-hydroxytetrahydrofuran is obtaned from butane-1,2,4-triol in yields of only about 60 mole %.

Since one molecule of water is formed on cyclization to hydroxytetrahydrofuran it was to be expected that the dehydration would be promoted by rapid removal of the water of reaction. Surprisingly, however, it has been found that both the selectivity and the rate of the synthesis reaction are increased by the presence of additional amounts of water. Thus, for example, an excess of 90 mole % or more of water in the feed to the dehydration reactor results in yields of hydroxytetrahydrofuran of from 96 to 100 mole %. Compared to the dehydration in the absence of water or presence of small amounts of water, the process according to the invention gives a reaction rate which is several times higher.

In the Example which follows, parts are by weight and bear the same relation to parts by volume as that of the kilogram to the liter.

EXAMPLE 40 parts of butane-1,2,4-triol, 10 parts of bleaching earth commercially available under the registered trademark Tonsil, Optimum FF (from Süd-Chemie, Munich, Federal Republic of Germany) and 0.01 part of sodium bicarbonate are introduced into a distillation flask equipped with a stirrer and a fractionating column (5 theoretical plates). 50 parts of water are then added (representing 7.4 moles per mole of butanetriol) and the mixture is heated to 165° C. A vigorous reaction starts at 150° C., and at 165° C. 20 parts per hour of butanetriol are converted to 3-hydroxytetrahydrofuran. The latter, together with water, issues at the top of the fractionating column, at a boiling point of about 130° C., and is taken off the reaction system as an aqueous solution. The butanetriol consumed, and the water evaporated, are replaced at the rate at which the reaction proceeds by feeding a 40% strength aqueous butanetriol solution into the flask. When 2,000 parts of butanetriol have been reacted, the rate of reaction is still 30% of the original rate of reaction. The reaction is then stopped or completed by introducing 100 parts of water over 5 hours into the distillation flask at 170° C. In addition to the bleaching earth employed there remains, in the distillation flask, about 0.5–1% by weight, based on butanetriol introduced, of higher-boiling products. Fractional distillation under reduced pressure using a column with 10 theoretical plates gives 3-hydroxytetrahydrofuran in a yield of more than 98 mole %, based on triol originally employed, the purity of the product, as determined by gas chromatography, being more than 99.8%.

We claim:

1. A process for the preparation of 3-hydroxytetrahydrofuran by the dehydration of butane-1,2,4-triol in a distillation vessel in the liquid phase over a catalyst at an elevated temperature, wherein a catalyst chosen from the group of the bleaching earths is used, wherein the dehydration is carried out in the presence of not less than 3 moles of water per mole of butane-1,2,4-triol and wherein a mixture of 3-hydroxytetrahydrofuran in water is distilled off and an aqueous solution of butane-1,2,4-triol, containing not less than 60% of water, is introduced at the same time to the distillation vessel.

2. The process of claim 1, wherein from 0.05 to 1% by weight, based on the bleaching earth, of an alkali metal carbonate or alkaline earth metal carbonate is added to the starting mixture.

3. The process of claim 1 wherein the dehydration is carried out at a temperature of from 150° to 200° C.

* * * * *